United States Patent
Wheelock et al.

(10) Patent No.: US 6,589,236 B2
(45) Date of Patent: *Jul. 8, 2003

(54) ASSEMBLY CONTAINING AN ELECTROLYTICALLY SEVERABLE JOINT FOR ENDOVASCULAR EMBOLIC DEVICES

(76) Inventors: E. Thomas Wheelock, 14188 Stanford Ct., Los Altos, CA (US) 94022; Erik T. Engelson, 401 Encinal Ave., Menlo Park, CA (US) 94025; Harold F. Carrison, 410 Dolores Ct., Pleasanton, CA (US) 94566

( * ) Notice: Subject to any disclaimer, the term of this patent is extended or adjusted under 35 U.S.C. 154(b) by 0 days.

This patent is subject to a terminal disclaimer.

(21) Appl. No.: 10/086,172

(22) Filed: Feb. 28, 2002

(65) Prior Publication Data

US 2002/0091380 A1 Jul. 11, 2002

Related U.S. Application Data

(63) Continuation of application No. 09/523,540, filed on Mar. 10, 2000, now Pat. No. 6,409,721, which is a continuation of application No. 09/026,373, filed on Feb. 19, 1998, now Pat. No. 6,077,260.

(51) Int. Cl.$^7$ ............................ A61B 18/14; A61B 17/00
(52) U.S. Cl. ........................ 606/32; 606/108; 606/191
(58) Field of Search ........................... 606/32–108, 191

(56) References Cited

U.S. PATENT DOCUMENTS

| 4,739,768 A | 4/1988 | Engelson |
|---|---|---|
| 4,884,575 A | 12/1989 | Sanders et al. |
| 4,994,069 A | 2/1991 | Ritchart et al. |
| 5,122,136 A | 6/1992 | Guglielmi et al. |
| 5,250,071 A | 10/1993 | Palermo |
| 5,354,295 A | 10/1994 | Guglielmi et al. |
| 5,423,829 A | 6/1995 | Pham et al. |
| 5,522,836 A | 6/1996 | Palermo |
| 5,540,680 A | 7/1996 | Guglielmi et al. |
| 5,549,624 A | 8/1996 | Mirigian et al. |
| 5,569,245 A | 10/1996 | Guglielmi et al. |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,634,942 A | 6/1997 | Chevillon et al. |
| 5,643,254 A | 7/1997 | Scheldrup et al. |
| 5,645,082 A | 7/1997 | Sung et al. |
| 5,645,558 A | 7/1997 | Horton |
| 5,669,905 A | 9/1997 | Scheldrup et al. |
| 5,733,294 A | 3/1998 | Forber et al. |
| 5,743,905 A | 4/1998 | Eder et al. |

(List continued on next page.)

FOREIGN PATENT DOCUMENTS

| WO | WO 97/48351 | 12/1997 |
|---|---|---|
| WO | WO 98/02100 | 1/1998 |
| WO | WO 98/04198 | 2/1998 |
| WO | WO 98/04315 | 2/1998 |

OTHER PUBLICATIONS

Sadato et al "Treatment of a spontaneous carotid cavernous fistula using an electrodetachable microcil" American J. of Neuroradiology, 1993, 14:334–336.

*Primary Examiner*—Lee Cohen

(57) ABSTRACT

This invention is an apparatus for the formation of occlusions in spaces in the human body, occluding such as thrombi in arteries, veins, aneurysms, vascular malformations and arteriovenous fistulas. In particular, it deals with a one piece assembly having an improved electrolytically erodable link to an occlusive member and further having an incorporated return electrode in the assembly. The occlusion-forming member is introduced to and is intended to remain at the desired occlusion site. The invention also relates to the joint itself. The invention further includes a method for introduction and electrolytic separation of the device.

7 Claims, 8 Drawing Sheets

U.S. PATENT DOCUMENTS

| | | |
|---|---|---|
| 5,800,454 A | 9/1998 | Jacobsen et al. |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,895,391 A | 4/1999 | Farnholtz |
| 5,911,717 A | 6/1999 | Jacobsen et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,062 A | 7/1999 | Purdy |
| 5,928,226 A | 7/1999 | Guglielmi et al. |
| 5,944,714 A | 8/1999 | Guglielmi et al. |
| 5,984,929 A * | 11/1999 | Bashiri et al. ............... 606/108 |
| 6,409,721 B1 * | 6/2002 | Wheelock et al. ............ 606/32 |

* cited by examiner

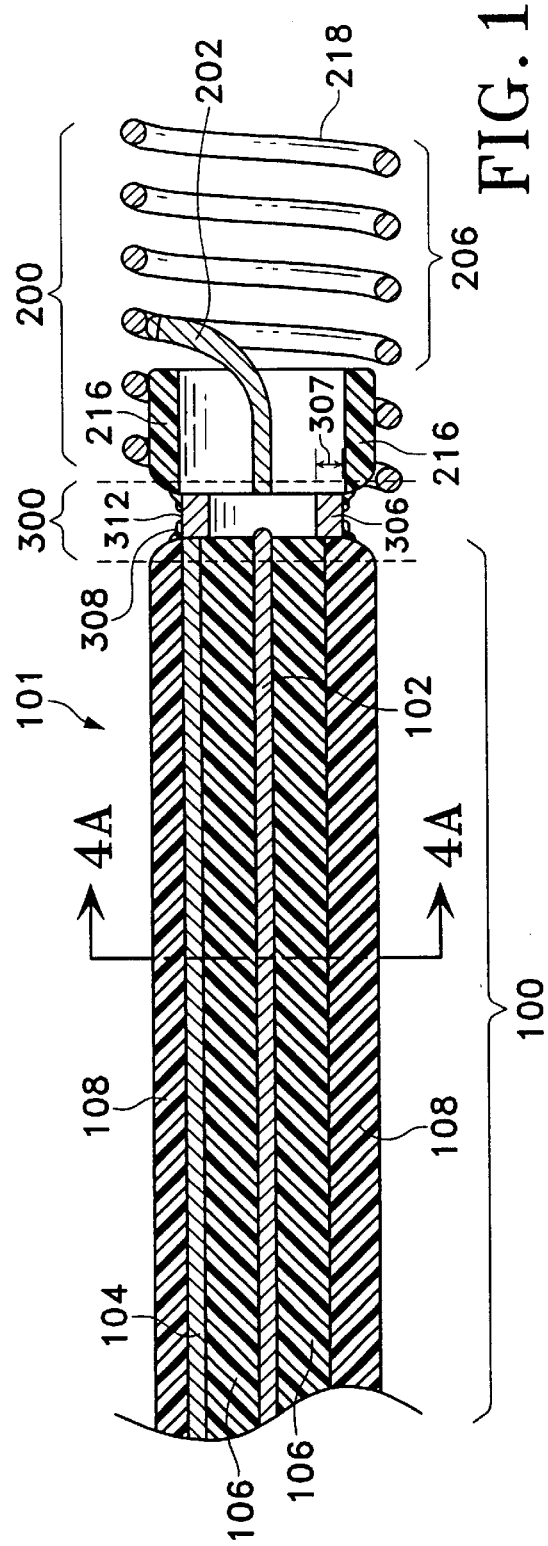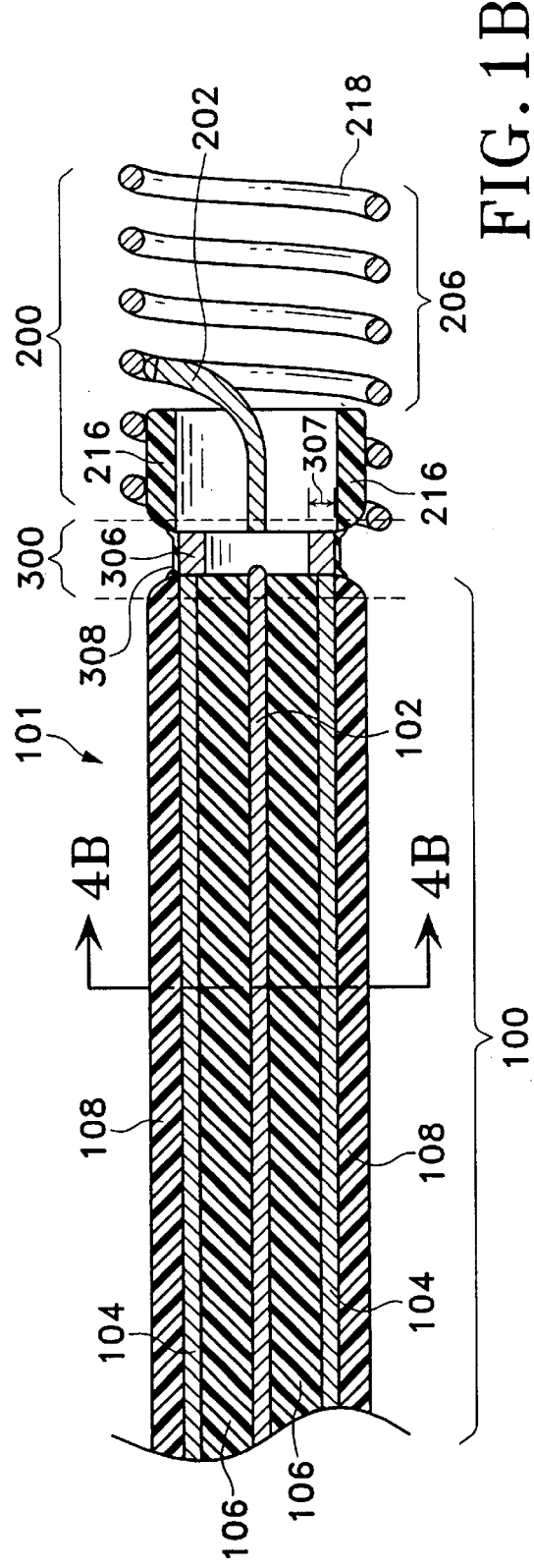

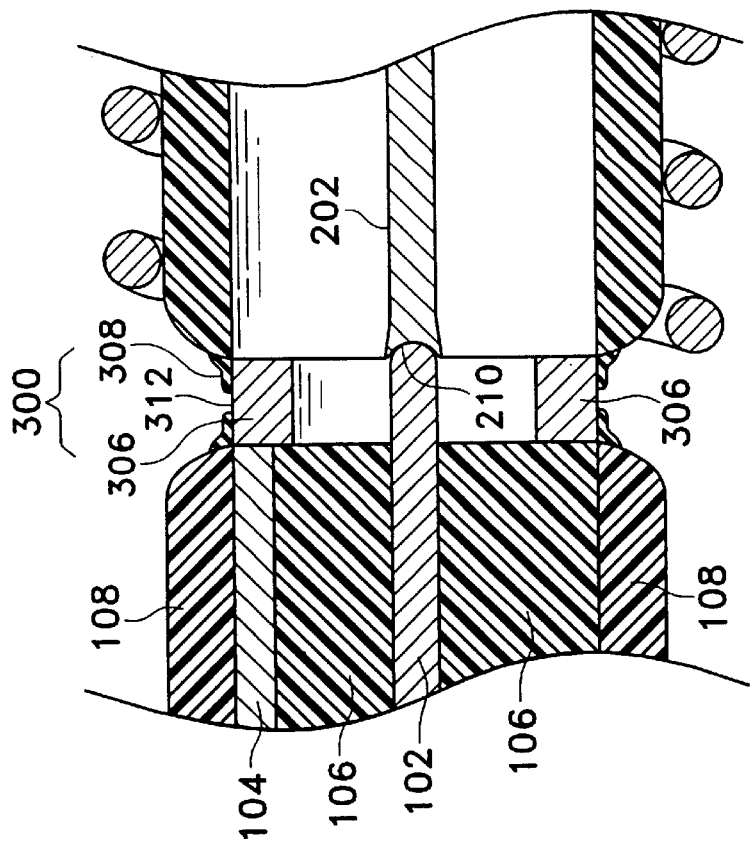
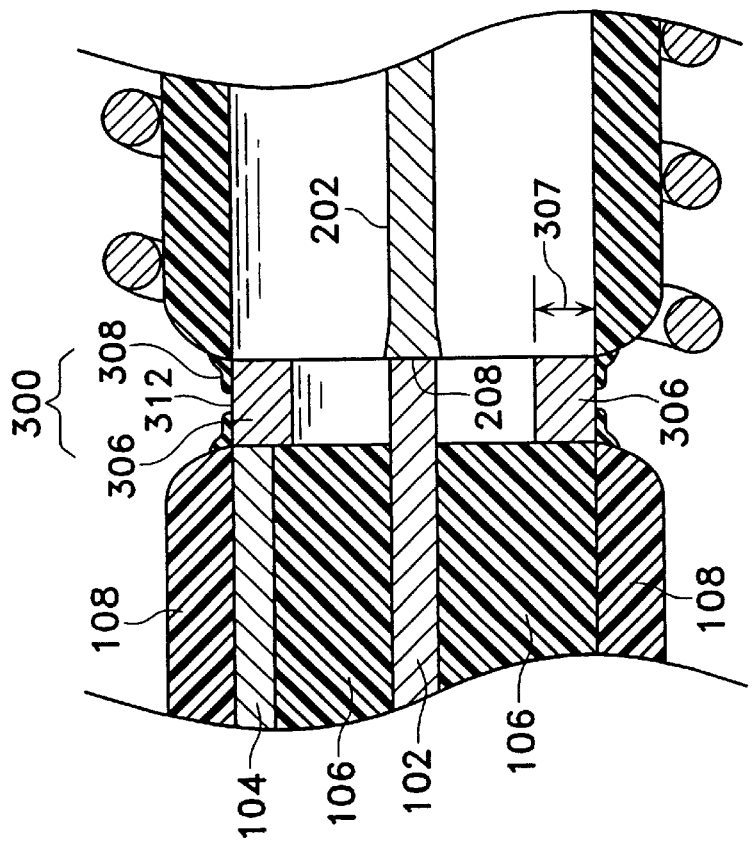

ASSEMBLY CONTAINING AN ELECTROLYTICALLY SEVERABLE JOINT FOR ENDOVASCULAR EMBOLIC DEVICES

CROSS-REFERENCE TO RELATED PATENT APPLICATION

This application is a continuation of U.S. patent application Ser. No. 09/523,540, filed on Mar. 10, 2000, now U.S. Pat. No. 6,409,721, which is a continuation of U.S. patent application Ser. No. 09/026,373, filed on Feb. 19, 1998, which issued as U.S. Pat. No. 6,077,260 on Jun. 20, 2000, both of which are hereby incorporated by reference herein, in their entireties.

FIELD OF THE INVENTION

This invention is an apparatus for the formation of occlusions in spaces in the human body, occluding such as thrombi in arteries, veins, aneurysms, vascular malformations and arteriovenous fistulas. In particular, it deals with a one piece assembly having an improved electrolytically erodable link to an occlusive member and further having an incorporated return electrode in the assembly. The occlusion-forming member is introduced to and is intended to remain at the desired occlusion site. The invention also relates to the joint itself. The invention further includes a method for introduction and electrolytic separation of the device.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by reference.

A still further approach is the least invasive and is additionally described in Guglielmi et al. It is the endovascular approach. In this approach, the interior of the aneurysm is entered by use of a catheter such as those shown in U.S. Pat. Nos. 4,884,575 and 4,739,768, both to Engelson. These patents describe devices utilizing core wires and catheters, respectively, which allow access to the aneurysm from remote portions of the body. By the use of catheters having very flexible distal regions and core wires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using catheters such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less favorable because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures is found in U.S. Pat. No. 4,994,069, to Ritchart et al. The device, typically a platinum/tungsten alloy coil having a very small diameter, may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture. Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as discussed above.

Guglielmi et al. teaches an embolism-forming device and procedure for using that device. Specifically, Guglielmi et al. fills a vascular cavity such as an aneurysm with an embolic device such as a platinum coil which has been endovascularly delivered. The coil is then severed from its insertion tool by the application of a small electric current. Desirably, the insertion device involves a core wire which is attached at its distal end to an embolic device by an electrolytic, sacrificial joint. Guglielmi et al. suggests that when the embolic device is a platinum coil, the coil may have a length ranging from 1 cm to 50 cm or longer as is necessary. Proximal of the embolic coil is an insulated core wire or pusher wire, often stainless steel in construction. The core wire is used to push the platinum embolic coil, obviously with great gentleness, into the vascular site to be occluded. The Guglielmi et al. patent shows a variety of ways to link the embolic coil to the core wire. For instance, the core wire is tapered at its distal end and the distal tip of the core wire is welded into the proximal end of the embolic coil. Additionally, a stainless steel coil is wrapped coaxially about the distal tapered portion of the core wire to provide column strength to the core wire. This coaxial stainless steel wire is joined both to the core wire and to the embolic coil. Insulation may be used to cover a portion of the strength-providing stainless steel coil. This arrangement provides for two regions which must be electrolytically severed before the embolic coil is severed from the core wire.

A still further variation found in Guglielmi et al. includes a thin, threadlike extension between the core wire core and the proximal end of the embolic coil. In this way, the core wire does not extend to the embolic coil, but instead relies upon a separately introduced extension.

A continuation-in-part of the Guglielmi et al. patent discussed above, U.S. Pat. No. 5,354,295, describes the use of mechanically detachable embolic devices as well as those which are electrolytically detachable. The embolic devices may be augmented with attached filaments. U.S. Pat. No. 5,540,680, a continuation of U.S. Pat. No. 5,354,295, further describes such mechanically and electrolytically detachable embolic devices. U.S. Pat. No. 5,569,245, a continuation-in-part of the U.S. Pat. No. 5,540,680 patent, adds several new aspects including a new method for electrocoagulation.

A further variation of the Guglielmi et al. device is one in which the distal tip of the stainless steel core wire is crimped onto the proximal end of the embolic device. A simple tapered stainless steel wire extends from the stainless steel pusher wire to the embolic coil.

Taki et al. have devised a variation of the Guglielmi detachable coil using a copper link between the core wire and the coil, described in Treatment of a Spontaneous Carotid Cavernous Fistula Using an Electrodetachable Microcoil, *American Journal of Neuroradiology*, Vol. 14 (1993).

U.S. Pat. Nos. 5,423,829 to Pham et al. and 5,624,449 to Pham et al. describe an electrolytically detachable vaso-occlusive device containing a discrete sacrificial link between the core wire and the vaso-occlusive device to allow clean and quick detachment from the core wire, reducing the possibility of multiple electrolysis sites. The use of extensive electrical insulation about the core wire and sacrificial link as well as the use of scoring on the insulation to focus electrolysis on a targeted, specific site on the link is also taught by Pham et al.

None of the noted procedures using electrolytically detachable embolic devices suggest the structure of the erodable link and related composite core wire described herein.

SUMMARY OF THE INVENTION

This invention is a device for forming an occlusion in the human body. Particularly, it is for forming a vascular occlusion. Generally, the device comprises a core wire having a distal tip, which distal tip may be introduced into the selected vascular site or cavity. The core wire is joined to the distal tip or embolic device in such a way that the vascular device may be electrolytically detached by application of a current to the core wire. The improvement involves the use of a discrete, erodable link between the composite core wire and the vascular implant device to allow clean and quick detachment from the composite core wire and the placement of the return electrode at the inventive assembly. Specifically the most desirable of the improved sacrificial joints is a narrow band which has been cut from a coating, e.g., a polymeric coating adherent to the metallic substrate, perhaps by laser cutting. Focused electrolysis produced at the erodable site as a result of a key improvement, two independent conductive layers within the composite core wire, increases electrolysis precision and efficiency by eliminating the need for a charged extracutaneous patch. This focused electrolysis also reduces the overall possibility of occurrence of multiple electrolysis sites and liberation of large particles from those sites. Further, placement of the return electrode of the inventive assembly removes the necessity of the prior art devices to place a return electrode on the skin of the patient and instead places the return electrode next to the erodable sacrificial joint in the body's ionic fluids.

BRIEF DESCRIPTION OF THE DRAWINGS

FIGS. 1A–1C, 2A, 2B, and 3 show side and partial longitudinal cross-sections of variations of the electrolytically susceptible, sacrificial link between a core wire and an embolic device of the present invention.

DETAILED DESCRIPTION OF THE INVENTION

This invention involves an assembly having a pusher, an electrolytically erodible joint, a distally located occlusion device, and a return electrode. These are two major variations of this inventive device. The first, discussed just below, utilizes the occlusion device as the return electrode. The second variation utilizes a specifically placed return electrode on the outer surface of the pusher.

Figure 4:
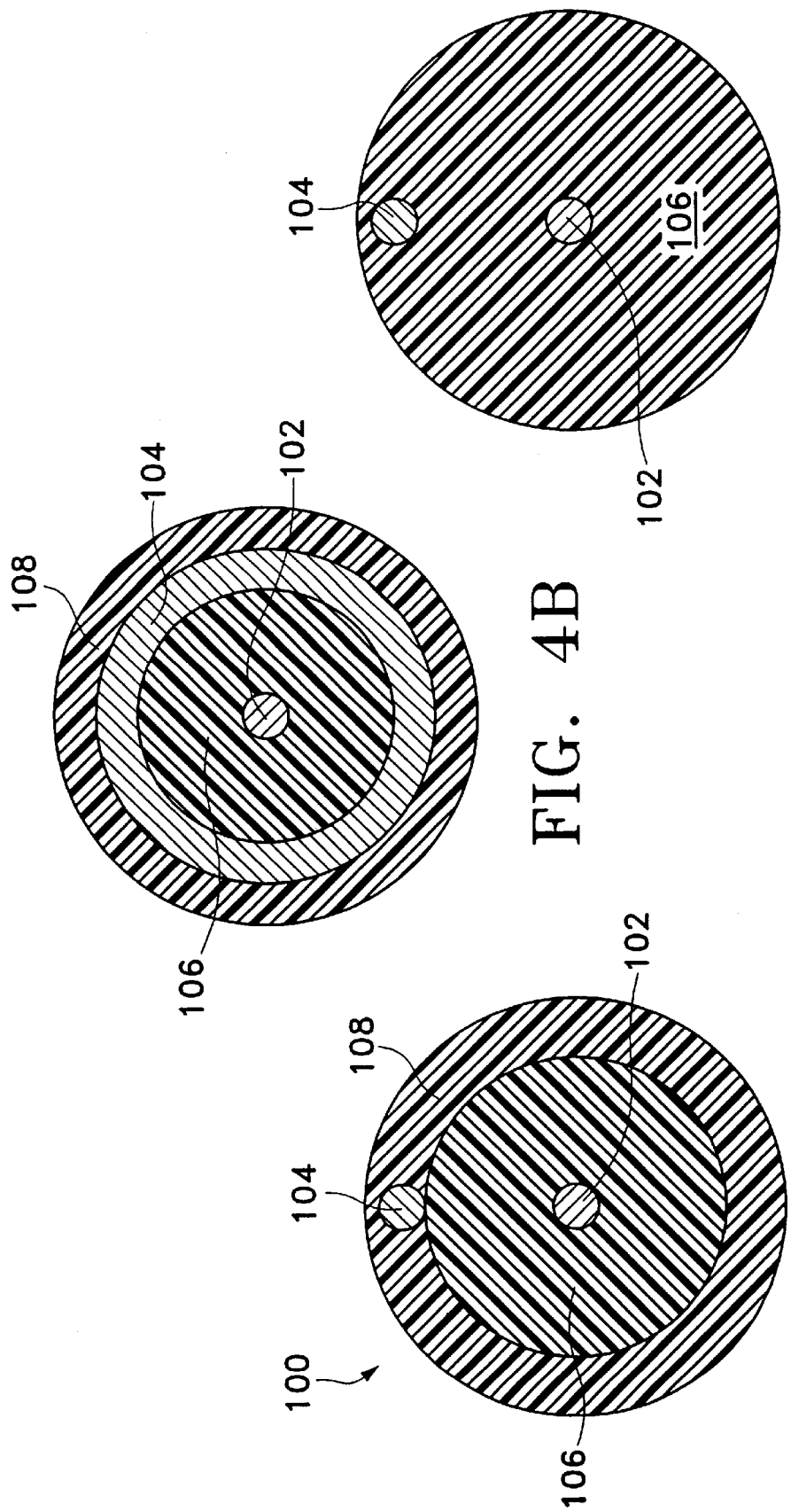
FIGS. 4A–4C show transverse cross sections of the variations shown in FIGS. 1A–1C, respectively.

FIG. 1A is a side view, in partial cross section, of one highly desirable variation of the inventive wire assembly (101). The variation in FIGS. 1A and 4A is made up of a composite core wire (100), an implant (200), and an electrolytically erodable junction (300) which serves as the temporary joint between the core wire (100) and implant (200).

In this variation, the composite core wire (100) comprises several elements. A first electrically conductive member (102) extends from the proximal end to the distal end of the core wire (100), and is capable of carrying electric current. This member (102) may comprise a tubular, multistrand, or braided structure. Preferably, conductive member (102) comprises a small electric wire lead running along the longitudinal axis of the core wire (100), as is shown in FIGS. 1A–1C and 4A–4C. A small diameter is preferred because overall flexibility of the wire assembly (101) is desired, and a large wire lead would possibly contribute excessive stiffness to the structure. Although the orientation of conductive member (102) along the longitudinal axis is not necessary, it is preferred because such positioning gives the overall core wire (100) more predictable mechanical behavior during twisting, flexing, and other such maneuvering.

Figure 1C:
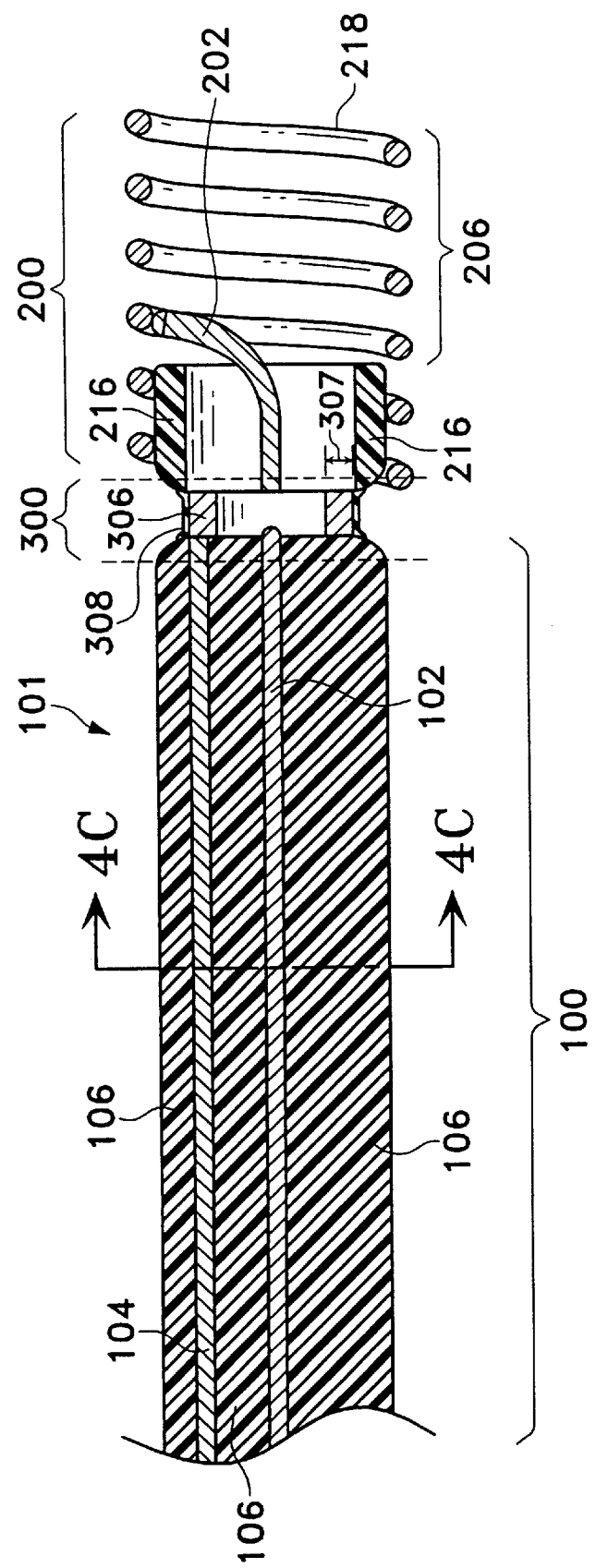

In the variations depicted in FIGS. 1A–1C, the distal end of the first electrically conductive member (102) is configured to protrude slightly from the distal end of the composite core wire (100). This configuration facilitates electrical contact with the implant (200). Generally speaking, electrically conductive member (102) is in electrical contact with implant (200). However, in the variations discussed herein, this first electrically conductive member (102) forms one of the two electrical leads which enable an operator to actuate the implant (200) detachment mechanism remotely. By "remotely", we mean that the operator is able to actuate the detachment mechanism from a position outside of the patient's body.

Also shown in FIGS. 1A–1C and 4A–4C is a second electrically conductive member (104). In each variation, this member (104) forms the other electrical lead which extends the length of the composite core wire (100) and enables the operator to remotely actuate implant detachment. Member (104) is also capable of carrying current, and is electrically insulated from the first electrically conductive member (102) so the two conductive members (102, 104) can carry current in opposite directions.

Highly desirable is the variation, depicted in FIGS. 1A and 4A, in which the second electrically conductive member (104) comprises a single strand electrically conductive lead which extends the length of the composite core wire (100), and is disposed along one aspect of a generally tubelike first electrically insulating member (106). This member (106) surrounds the first electrically conductive member (102), electrically insulates the two conductive members (102, 104) from each other, and directly contacts each of the two conductive members (102, 104). The core wire (100) further includes a second electrically insulating member (108) which surrounds both the second electrically conductive member (104) and the first electrically insulating member (106) and electrically insulates them from surrounding body fluids, as shown in FIG. 4A.

Alternatively, as depicted in FIGS. 1B and 4B, the second electrically conductive member (104) may be a tubular structure which extends the length of the composite core wire (100), and surrounds a generally tubelike first electrically insulating member (106). This member (106) is configured to surround the first electrically conductive member (102), electrically insulate the two conductive members (102, 104) from each other, and directly contact each of the two conductive members (102, 104). As with the variation described above, this core wire (101) further includes a second electrically insulating member (108) which surrounds both the second electrically conductive member (104) and the first electrically insulating member (106) and electrically insulates them from surrounding body fluids, as shown in FIG. 4B.

Further, as depicted in FIGS. 1C and 4C, the second electrically conductive member (104) may be a single-strand, electrically conductive lead which extends the length of the composite core wire (100) as in the preferred variation, but the two conductive members (102, 104) are electrically insulated from each other and surrounding body fluids by a single electrically insulating member (106) having two lumens configured to contain the two electrically conductive members, as shown in FIG. 4C. The electrically insulating members of these three variations are generally tubelike in geometry, and are preferably comprised of flexible polymer materials as is discussed below.

Also depicted in FIGS. 1A–1C is an implant (200). This implant (200) can have various configurations as long as the required elements for the inventive detachment mechanism are in place. In this configuration, the inventive implant (200) is electrically isolated from second electrically conductive member (104) and erodible ring (306) but in electrical contact with first electrically conductive member (102). One way in which this may be accomplished is by the use of a third electrically conductive member (202). This third electrically conductive member (202) is insulated from the second electrically conductive member (104), but is in electrical contact with the first electrically conductive member (102) before implant release, and is in electrical contact with an exposed area (206) of the implant which is in electrical contact with surrounding body fluids. FIGS. 1A–1C depict a preferred coil implant (218) which has an insulating layer (216) electrically isolating it from the second electrically conductive member (104). The entire distal portion of the coil (218) serves as the exposed area (206), as it is in direct electrical contact with surrounding body fluids.

The proximal portion of the third electrically conductive member (202) is configured to establish electrical contact with the first electrically conductive member (102) when the implant (200) and core wire (100) are urged together, while it is also configured to easily relinquish such electrical contact when the junction (300) between the implant (200) and the core wire (100) is eroded, thus allowing the implant (200) and core wire (100) to move apart. FIG. 2A depicts one contact geometry in which the proximal end of the third electrically conductive member (202) is configured to have a simple flat surface (208) perpendicular to the longitudinal axis of the core wire (100). When the implant and core wire are in contact with each other, as is the case when the junction (300) therebetween is intact, the protruding distal end of the first electrically conductive member (102) is in contact with the flat surface (208) of the proximal third electrically conductive member (202).

FIG. 2B depicts a more preferred contact geometry, wherein the proximal end of the third electrically conductive member (202) forms a socket (210) configured to at least partially surround the protruding distal end of the first electrically conductive member (102) when the core wire (100) and implant (200) are in contact with each other. This contact geometry is preferred because it is believed to establish better electrical contact between the two conductive members (102, 202); more surface area is shared at the junction.

As discussed in passing above, electrolytically erodable junction (300) between the implant (200) and composite core wire (100) is also shown in FIGS. 1A–1C. This junction is configured to controllably erode and release the implant into the desired body cavity. In the depicted variation, the junction (300) preferably comprises an electrically conductive erodable ring (306) having an inner diameter and an outer diameter. The difference between the inner and outer diameters, or ring thickness (307), desirably is large enough to meet structural requirements yet small enough to erode quickly. The electrically conductive erodable ring (306) is in electrical contact with the second electrically conductive member (104) and surrounding body fluids, and is electrically insulated from the first and third electrically conductive members (102, 202) as well.

Preferably, the electrically conductive erodable ring (306) has a narrow range of circumferential contact with surrounding body fluids, so that erosion will be focused. By "focused" we mean that erosion will be limited to a narrow circumferential band, rather than a broad one; this will result in quicker erosion through the thickness of the electrically conductive erodable ring (306). In the preferred variation, a ring insulating outer layer (308) may be disposed around the erodable ring (306) in a configuration that would electrically isolate it from surrounding body fluids; this ring insulating outer layer (308) may then be scored or cut to produce a very narrow circumferential band (312) exposing the ring (306) to surrounding body fluids. The scoring may be made physically using a sharp object, abrasive spray techniques, or more preferably, may be done with a laser or like focused energy source.

Figure 6A:
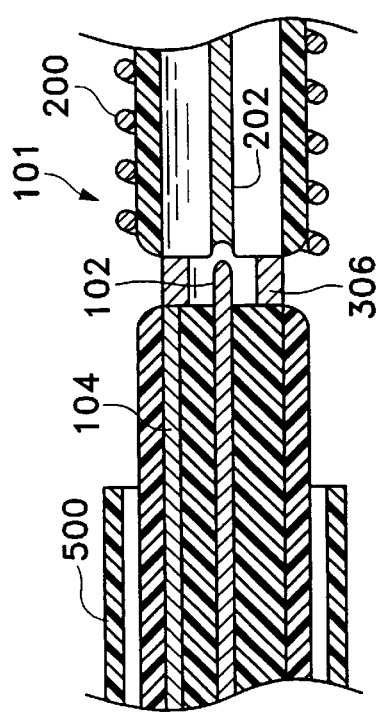
FIGS. 6A–6C schematically depict the method for deploying the vasoocclusive device using the inventive sacrificial link shown in FIG. 1.
Figure 6B:
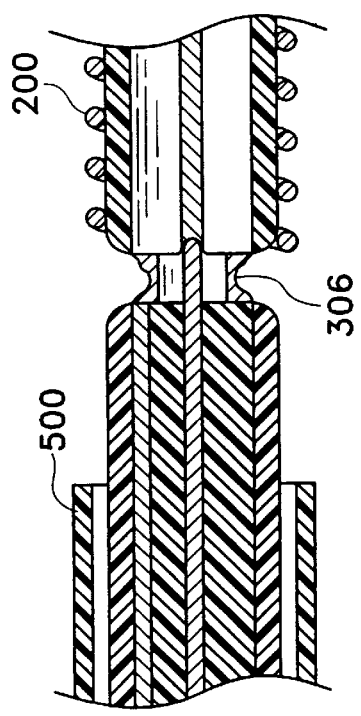
Figure 6C:
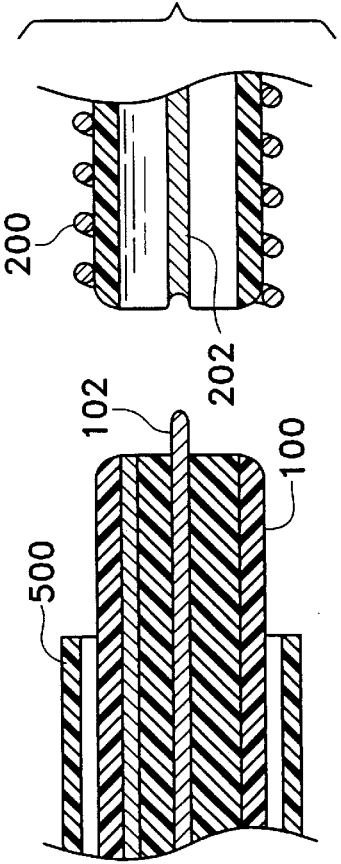

FIGS. 6A, 6B, and 6C illustrate the method by which controllable implant detachment is accomplished using the aforementioned preferred variation of the inventive wire assembly depicted in FIGS. 1A and 4A (without layer (308)). FIG. 6A depicts the wire assembly (101) extending out of the delivery catheter (500) and into a desirable implantation position. In FIG. 6B, the operator of the device, deciding to controllably detach the implant (200) in this position, has applied a potential difference, or "voltage", across the first electrically conductive member (102) and the second electrically conductive member (104). Since it is desirable to electrolytically erode the electrically conductive erodable ring (306) which is in electrical contact with the second electrically conductive member (104), a positive polarity is applied to the second electrically conductive member (104), and a negative polarity is applied to the first electrically conductive member (102). The potential difference across the two conductive members (102, 104) may range in amplitude from 0 to 5 volts. Preferably a potential difference of no more than 5 volts is applied.

Because the electrically conductive erodable ring (306) is in electrical contact with body fluids and the second electrically conductive member (104), it assumes a positive charge in an ionic medium. Since the exposed area (206) is in contact with body fluids and the third electrically conductive member (202), which is itself in contact with the first electrically conductive member (102), the exposed area (206) assumes a negative charge in an ionic medium. In the preferred variation, the electrically conductive erodable ring (306) is comprised of a metal less noble that that which comprises the exposed area (206) of the implant. Given these conditions, galvanic corrosion of the electrically conductive erodable ring (306) occurs and the ring material is eroded away, as shown in FIG. 6B. When the entire thickness of the ring (306) has been eroded, the implant (200) will no longer be physically constrained to the core wire (100), and the core wire (100) can be pulled away, breaking contact between the first electrically conductive member (102) and the third electrically conductive member (202), as shown in FIG. 6C. The core wire (100) and delivery catheter (500) can then be fully withdrawn, leaving the deployed implant (200).

Figure 3:
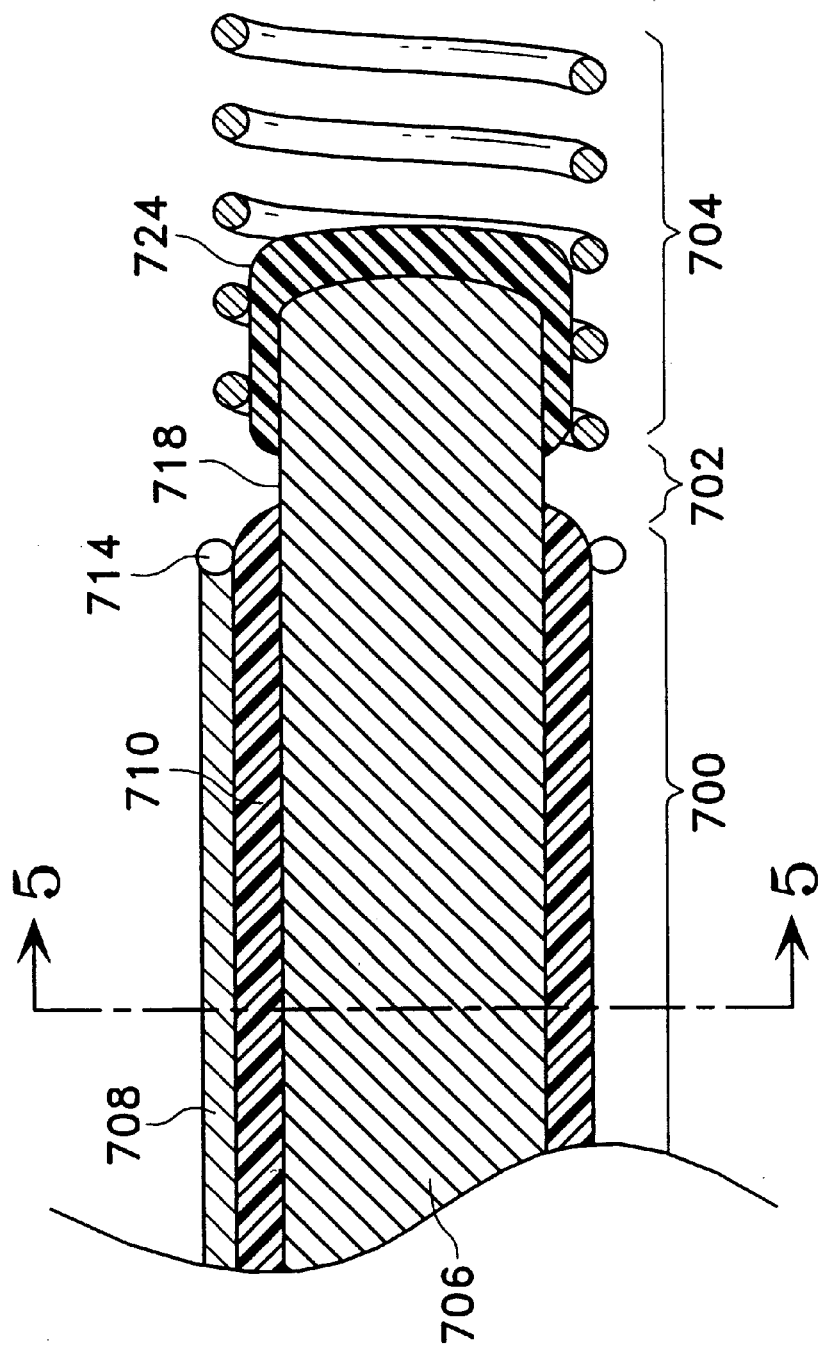
Figure 5:
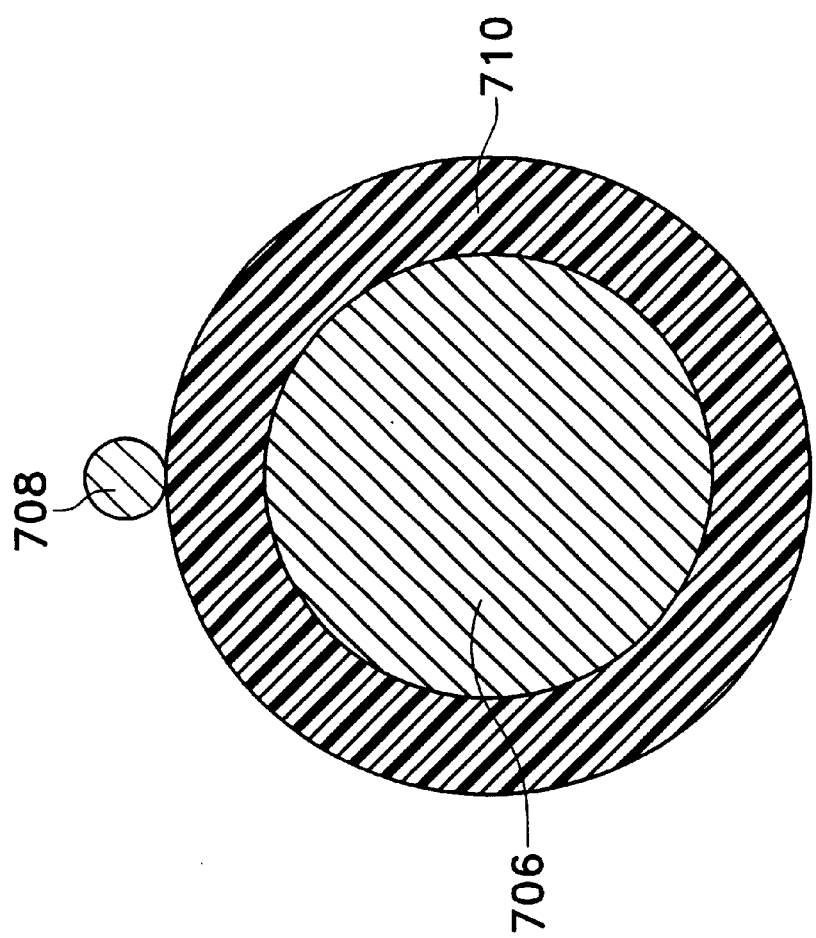
FIG. 5 shows a transverse cross section of the variation shown in FIG. 3.

FIGS. 3 and 5 depict the second variation of the inventive wire assembly. This variation also has three primary components: a composite core wire (700), an electrolytically erodable junction (702), and an implant (704). Preferably, the implant (704) comprises a coil which is generally comprised of a material more noble than that from which the second electrically conductive member (708) is comprised. The composite core wire (700), as shown in FIG. 3, has a first electrically conductive member (706) which extends from the proximal end of the core wire (700) through the distal end of the core wire. This conductive member (706) may comprise a multi-strand wire configuration, a tubular configuration, or a single solid wire. Preferably, this conductive member (706) is a single tapered solid wire. A second electrically conductive member (708) also runs the length of the core wire (700), as shown in FIGS. 3 and 5. A first electrically insulating member (710), configured to directly contact both first and second electrically conductive members (706, 708), electrically insulate them from each other, and to electrically insulate the first electrically conductive member (706) from surrounding body fluids is also shown in FIG. 3. Since this insulating member (710) is designed to electrically isolate the first electrically conductive member (706) from both surrounding fluids and the second electrically conductive member (708), it typically has a generally tubular geometry.

The second electrically conductive member (708) of this variation may be a tubular member or coating which surrounds the first electrically insulating member (710). More preferably, the second electrically conductive member (708) comprises a single electrical lead extending along one aspect of the generally tubular first electrically insulating member (710) from the proximal end of the core wire (700) to the distal end, wherein the second electrically conductive member (708) is configured to form a loop (714) around the distal end of the first electrically insulating member (710). The single electrical lead configuration, depicted in FIG. 5, is believed to contribute less overall stiffness to the core wire (700) than would a tubular conductive member or conductive coating, thus its preferability.

In this variation, the implant (704) is held in position at the distal end of the wire assembly by an electrolytically erodable junction (702), as shown in FIG. 3. This junction (702) generally comprises an electrically conductive member which is in direct electrical contact with the surrounding body fluids and the first electrically conductive member (706), is structurally connected to the implant (704), and is electrically insulated from the second electrically conductive member (708) of the core wire (700). The electrolytically erodable junction (702) typically comprises an extension of the first electrically conductive member (706) and the first electrically insulating member (710), with a score or cut through the insulating member to expose a narrow band (718) of the conductive member to surrounding body fluids. This narrow circumferential band of body fluid exposure is desirable for focused erosion as described above.

Figure 7A:
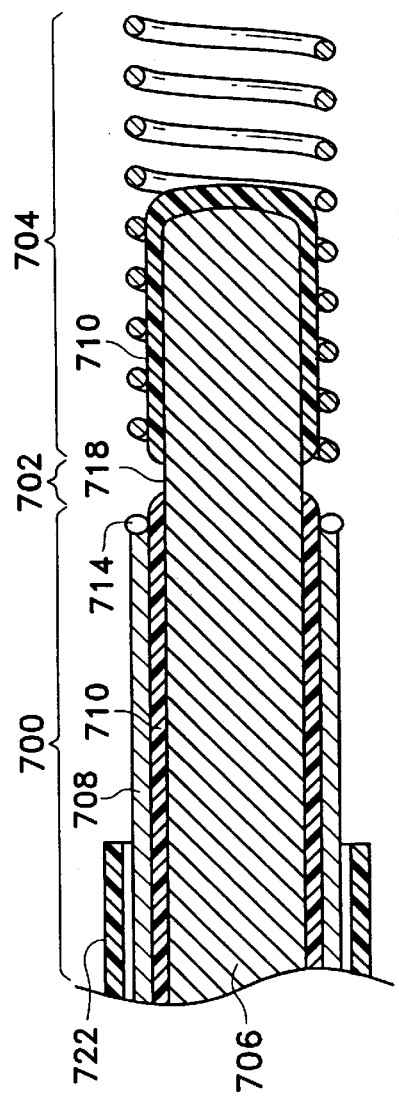
FIGS. 7A–7C schematically depict the method for deploying the vasoocclusive device using the inventive sacrificial link shown in FIG. 3.
Figure 7B:
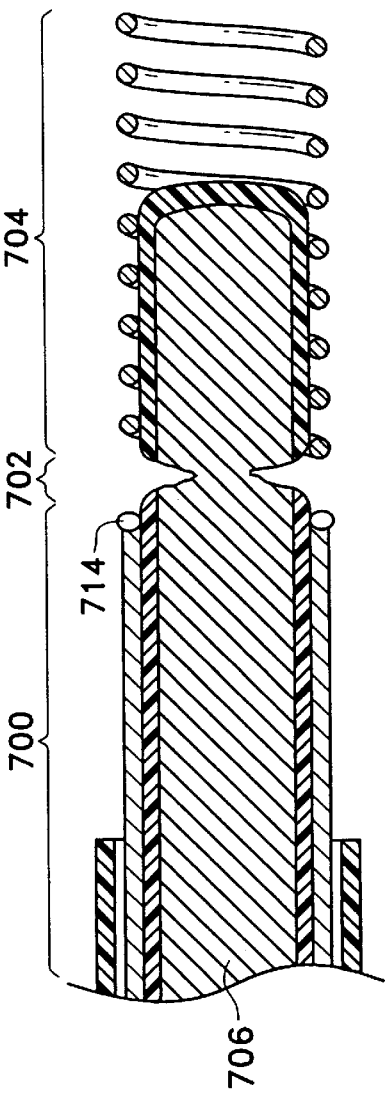
Figure 7C:
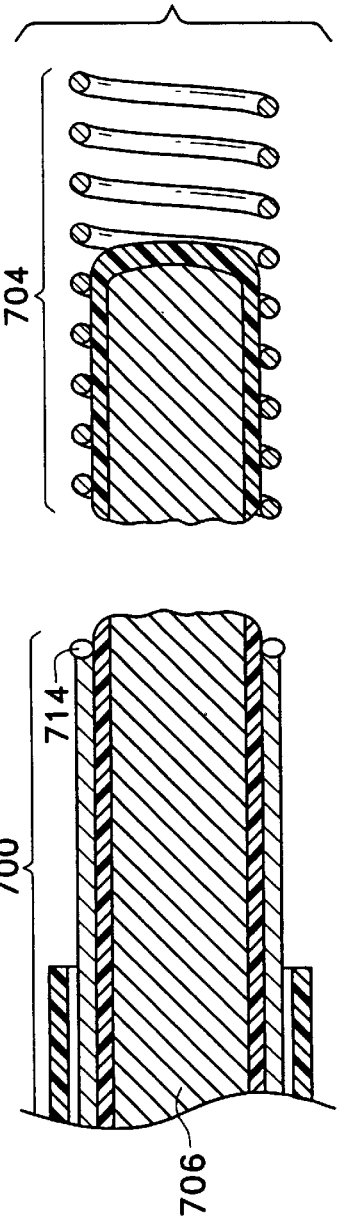

FIGS. 7A, 7B, and 7C depict a controlled deployment process using this variation of the inventive wire assembly. FIG. 7A depicts the wire assembly extending out of the delivery catheter (722) and into a desirable implantation position. In FIG. 7B, the operator of the device, deciding to controllably detach the implant (704) in this position, has applied a potential difference, or "voltage", across the first electrically conductive member (706) and the second electrically conductive member (708). Since it is desirable to electrolytically erode the distal extension of the first electrically conductive member (706) below the narrow band (718) of exposure to body fluid, a positive polarity is applied to the first electrically conductive member (706), and a negative polarity is applied to the second electrically conductive member (708). The potential difference across the two conductive members (706, 708) may range in value from 0 to about 5 volts. Preferably, a potential difference of not more than 5 volts is applied.

Since the narrow circumferential band (718) of the distal extension of the first electrically conductive member (102) is in electrical contact with body fluids around that circumferential band (718), it assumes a positive charge in an ionic medium. The second electrically conductive member (708) assumes a negative charge in an ionic medium. In the preferred variation, the first electrically conductive member (706) is comprised of a metal less noble that that which comprises the second electrically conductive member (708). Given these conditions, galvanic corrosion of the first electrically conductive member (706) occurs at the circumferential region (718) of body fluid contact, and the conductive material is eroded away as shown in FIG. 7B.

The material comprising the implant (704) in the preferred variation will not erode due either to an implant insulating layer (724) being in place to electrically insulate the proximal end of the implant (704) from surrounding body fluids, as shown in FIG. 3, or due to the fact that the material comprising the implant may be higher in the electromotive series than that which comprises the first conductive member (706). The preferred variation of the implant (704) has a proximal implant insulating layer (724) and is comprised of a material which is either an insulator or is more noble that the material which comprises the first conductive member. When the entire thickness of the member has been eroded, the implant (704) will no longer be physically constrained to the core wire (700), and the core wire (700) can be pulled away from the implant (704), as shown in FIG. 7C. The core wire (700) and delivery catheter (722) can then be fully withdrawn, leaving the deployed implant (704).

The materials used for the various electrically insulating members and layers discussed herein may be flexible polymeric coatings or layers such as polyfluorocarbons, polyurethane, polyethylene, polypropylene, polyimides, silicone polymers, or other suitable polymeric materials. Such polymeric materials are generally flexible, have good electrical insulation properties, and are amenable to sharp edge or laser scoring. The implant (704) may be a biocompatible metal or polymer but generally is comprised of a metal such as platinum or nickel-titanium, or alloys thereof.

Many alterations and modifications may be made by those having ordinary skill in the art without departing from the spirit and scope of the invention. The illustrated variations have been used only for the purposes of clarity and should not be taken as limiting the invention as defined by the following claims.

What is claimed is:

1. A process for forming an occlusion in a body cavity, comprising:

advancing an implant to a body cavity, said implant being detachably connected to a composite core wire via an electrolytically erodable junction, said composite core wire comprising a first conductive member selectively movable with respect to the composite core wire, said implant comprising a second conductive member separated from said first conductive member, said junction being electrically insulated from said first conductive member and said second conductive member, said implant forming a return path for current provided to said first conductive member through ionic body fluids;

advancing said first conductive member into a separable electrical contact with said second conductive member when said implant is at a desired location; and electrolytically eroding said junction to separate said second conductive member from said first conductive member and release said implant from said composite core wire.

2. The process of claim 1, wherein said implant comprises a coil.

3. The process of claim 2, wherein said implant comprises a platinum alloy coil.

4. The process of claim 1, wherein said first conductive member protrudes distally from a distal end of said insulating member during the first advancing step.

5. The process of claim 1, comprising electrolytically eroding said junction by imposing a current to said junction via said composite core wire.

6. The process of claim 1, wherein said composite core wire further comprises a third conductive member electrically insulated from the first conductive member and in electrical contact with said junction.

7. The process of claim 6, comprising electrolytically eroding said junction by applying a potential difference between said first conductive member and said third conductive member.

* * * * *

UNITED STATES PATENT AND TRADEMARK OFFICE
CERTIFICATE OF CORRECTION

PATENT NO.    : 6,589,236 B2
DATED         : July 8, 2003
INVENTOR(S)   : E. Thomas Wheelock et al.

It is certified that error appears in the above-identified patent and that said Letters Patent is hereby corrected as shown below:

Title page,
Item [54], Title, delete "VASO-OCCLUSION APPARATUS HAVING A MECHANICALLY EXPANDABLE DETACHMENT JOINT AND A METHOD FOR USING THE APPARATUS" and insert therefore -- PROCESS FOR FORMING AN OCCLUSION IN A BODY CAVITY --

Signed and Sealed this

Twenty-ninth Day of June, 2004

JON W. DUDAS
*Acting Director of the United States Patent and Trademark Office*